United States Patent [19]

Wargo et al.

[11] Patent Number: 5,426,222

[45] Date of Patent: Jun. 20, 1995

[54] METHOD FOR THE PREPARATION OF IODONIUM SALTS

[75] Inventors: Scott E. Wargo, Hummelstown, Pa.; John P. Cannady, Midland, Mich.

[73] Assignee: Dow Corning Corporation, Midland, Mich.

[21] Appl. No.: 292,149

[22] Filed: Aug. 17, 1994

[51] Int. Cl.$^6$ .................. C07C 53/15; C07C 53/16
[52] U.S. Cl. ........................... 562/602; 568/6; 568/13
[58] Field of Search ............. 562/602; 568/6, 13

[56] References Cited

U.S. PATENT DOCUMENTS

| | | | |
|---|---|---|---|
| 4,108,747 | 8/1978 | Crivello | 204/159.18 |
| 4,125,555 | 11/1978 | Reineke | 260/456 |
| 4,310,469 | 1/1982 | Crivello | 260/446 |
| 4,348,525 | 9/1982 | Koser et al. | 546/346 |
| 4,399,071 | 8/1983 | Crivello et al. | 260/440 |
| 4,482,679 | 11/1984 | Irving | 525/327.3 |
| 4,513,137 | 4/1985 | Koser et al. | 546/14 |
| 4,518,676 | 5/1985 | Irving | 522/15 |
| 4,554,360 | 11/1985 | Yamazaki et al. | 549/261 |
| 4,593,052 | 6/1986 | Irving | 522/31 |
| 4,786,441 | 11/1988 | Miller | 260/513 |
| 4,826,635 | 5/1989 | Koser et al. | 562/45 |
| 5,066,795 | 11/1991 | Umemoto et al. | 540/1 |

FOREIGN PATENT DOCUMENTS 4142327 12/1991 European Pat. Off. ........ C07F 7/08
0562922 3/1993 European Pat. Off. ... C09D 183/06

OTHER PUBLICATIONS

"Photochemistry of Diaryliodonium Salts" J. L. Dektar, N. P. Hacker, J. Organ. Chem. 1990 pp. 639–647.
"A Convenient Preparation of Diaryliodonium Triflates", Kitamura, Matsuyuki, Nagata, Furuki, Taniguchi, Synthesis Oct. 1992.
"Improved Preparation of Diaryliodonium Triflates", Kitamura, Matsuyuki Taniguchi, SYNTHESIS Feb. 1994.

Primary Examiner—Arthur C. Prescott
Attorney, Agent, or Firm—Timothy J. Troy

[57] ABSTRACT

The present invention relates to an improved method for the preparation of iodonium salts. More specifically, the present invention relates to an improved method for the production of symmetric or asymmetric diaryliodonium triflate (trifluoromethane sulfonate) salts. The diaryliodonium salts of the present invention are useful as photoacid catalysts for use in acid-sensitive polymerization and in curing systems such as radiation curable release coating compositions.

20 Claims, No Drawings

METHOD FOR THE PREPARATION OF IODONIUM SALTS

BACKGROUND OF THE INVENTION

The present invention relates to an improved method for the preparation of iodonium salts. More specifically, the present invention relates to an improved method for the production of symmetric or asymmetric diaryliodonium triflate (trifluoromethane sulfonate) salts. The diaryliodonium salts of the present invention are useful as photoacid catalysts for use in acid-sensitive polymerization and in curing systems such as radiation curable release coating compositions.

Iodonium salts and methods for their preparation have been described in the art. For example, Crivello, in U.S. Pat. No. 4,108,747 discloses cationically polymerizable compositions containing an organic material such as epoxides, vinyl ethers, and N-vinyl compounds and an effective amount of aryl onium trifluoromethane sulfonate salts such as triphenyl sulfonium trifluoromethane sulfonate and diphenyliodonium trifluoromethane sulfonate. These curable compositions are disclosed as being polymerizable under ultraviolet radiation.

Reineke, in U.S. Pat. No. 4,125,555, discloses trifluoromethanesulfonate esters which promote char formation in polymer compositions containing a monovinylidene aromatic monomer such as styrene and an ethylenically unsaturated carboxylic anhydride such as maleic anhydride. A method for the preparation of these trifluoromethanesulfonate esters is also described.

Crivello, in U.S. Pat. No. 4,310,469, teaches that epoxy monomers or prepolymers can be cationically polymerized by the use of certain radiationssensitive aromatic halonium salts. The radiation sensitive aromatic salts are disclosed as being diaryliodonium salts, and the radiation curable compositions are taught as being useful as sealants, coating compounds, and encapsulants.

Crivello, in U.S. Pat. No. 4,399,071 discloses a method for making diaryliodonium salts which are useful as photoinitiators for a variety of cationic polymerizable organic materials. In this method an aromatic iodo compound is reacted with an aryl organic aromatic compound in the presence of a peroxy organic acid and an organic sulfonic acid.

Miller, in U.S. Pat. No. 4,786,441 discloses a method for the preparation of iodonium and sulfonium triflates. In this method it is taught that the iodonium or sulfonium triflate is prepared by dissolving or slurring an iodonium or sulfonium halide in an organic solvent such as methylene chloride and reacting it with a trimethylsilyl triflate.

Dektar and Hacker, Journal of Organic Chemistry, 55, 639-647 (1990) discuss the photochemistry of diaryliodonium salts. Specifically, the photochemistry of diphenyl- and bis(4-methylphenyl)iodonium salts was investigated by product analysis, measurement of acid, and determination of the consumption of the iodonium salts. The similarities and differences between diaryliodonium and triarylsulfonium photochemistry is also described.

Umemoto et al. in U.S. Pat. No. 5,066,795 discloses (perfluoroalkyl)dibenzonium salts and a method for their preparation. These compounds are described as being useful as reagents for introducing perfluoroalkyl groups into various organic compounds.

Kitamura et al., Synthesis, 945-946, (1992), discloses a reagent prepared from iodosylbenzene and trifluoromethanesulfonic acid which reacts with aromatic compounds to give diaryliodonium triflates in good yields. The high reactivity of the reagent prepared is also disclosed. In this method a mixture of iodosobenzene and trifluoromethane sulfonic acid is made at 0° C. and is then further contacted with the desired aromatic substrate. However, iodosobenzene can only be prepared by hydrolysis of iodobenzenediacetate. In contrast, the method of the instant invention is easier to practice and employs more available starting materials. Furthermore, the method of the instant invention treats iodoarenedicarboxylates with strong acids such as trifluoromethanesulfonic acid which leads to the formation of bonded dimers however, unexpectedly, these dimers react to form desired monomeric products.

Herzig, in German Patent Publication No. DE 4142327 teaches silane containing iodonium salts and a process for their preparation. These iodonium salts are disclosed as being suitable as photoinitiators for polymerizing cationically polymerizable organic substances such as epoxides, vinyl ethers, epoxy group containing organopolysiloxanes, alkenyloxy group (such as vinyloxy or propenyloxy) containing organopolysiloxanes, and olefins. However, none of the references described hereinabove disclose the unique method of preparing diaryliodonium salts of the instant invention.

SUMMARY OF THE INVENTION

The present invention relates to a method of making diaryliodonium trifluoromethane sulfonate salts which comprises contacting a mixture of iodoaryldicarboxylate with a molar equivalent of trifluormethanesulfonic acid in a non-aromatic solvent to form a homogeneous solution at temperatures of below 0° C. to 100° C. depending on the liquid range of the solvent and mixtures. The method of the instant invention further comprises contacting the homogenous solution prepared above with a molar equivalent of a molecule containing at least one aromatic nucleus being at most pentasubstituted (having at least one unsubstituted hydrogen attached to the aromatic nucleus) at temperatures of below 0° C. to 100° C. depending on the liquid range of the solvent and mixtures. The pure compounds are isolated by removing the reaction solvent and adding a non-solvent to the residue and triturating until solidification occurs.

The compounds prepared by the method of the instant invention are suitable for use with polymerizable or curable compounds such as vinyl ether functional siloxane polymers, vinyl functional siloxanes, organic vinyl ethers, and olefins to afford radiation curable compositions.

It is an object of this invention to provide an improved method for the preparation of diaryliodonium trifluoromethane sulfonate salts.

It is also an object of this invention to provide a method for preparing diaryliodonium trifluoromethane sulfonate salts which is easier to practice and employs more available starting materials.

It is an additional object of this invention to provide a method for preparing diaryliodonium salts which results in improved yields while avoiding stringent reactant requirements and reaction conditions.

It is a further object of this invention to provide diaryliodonuim salt compounds which are advantageously employed with polymerizable or curable compounds such as vinyl ether functional siloxane polymers, vinyl functional siloxanes, organic vinyl ethers, and olefins to afford effective radiation curable compositions.

These and other features, objects and advantages of the present invention will be apparent upon consideration of the following detailed description of the invention.

DETAILED DESCRIPTION OF THE INVENTION

The present invention relates to a method for the preparation of iodonium salts, the method comprising the steps of: (I) mixing (A) substituted or unsubstituted iodoarene dicarboxylates and (B) a solvent selected from the group consisting of acetic acid, chlorinated hydrocarbons, and polar aprotic solvents, (II) adding to the mixture of (I) an acid (C) selected from the group consisting of perfluoroalkylsulfonic acids, hexahalometallic acids, hexahalometalloidic acids, tetrahaloboronic acids, tetrakis(perfluoroaryl)boronic acids, and tetrakisperfluoroalkylsulfonatoboronic acids at a temperature of at least $-20°$ C. to form a homogenous reaction mixture; (III) reacting with the homogenous reaction mixture of (II) a compound (D) selected from the group consisting of benzene, alkyl substituted benzenes, aryl substituted benzenes, arylalkyl substituted benzenes, alkoxy substituted benzenes, arylalkoxy substituted benzenes, and halobenzenes for at least 30 minutes; and (IV) stripping off solvent from the mixture of (III).

Compound (A) is a substituted or unsubstituted iodoarene dicarboxylate. The iodoarene dicarboxylate of Step (I) of the method of the instant invention is preferably a compound having the general formula $R'_aArI(O_2CR'')_2$ wherein $R'$ is selected from the group consisting of monovalent hydrocarbon or halohydrocarbon radicals free of aliphatic unsaturation and having from 1 to 40 carbon atoms, halogens, $NO_2$, $CN$, $COOH$, $SO_3H$, alkoxy radicals, nitro substituted groups, nitrile substituted groups, carboxylic acid substituted groups, sulfonic acid substituted groups, alkoxy substituted groups, $R''$ is a monovalent hydrocarbon or halohydrocarbon radicals free of aliphatic unsaturation and having from 1 to 20 carbon atoms, a has a value of from 0 to 5, and Ar is an arene having from 6 to 40 carbon atoms.

The group $R'$ can be a monovalent hydrocarbon or halohydrocarbon radical free of aliphatic unsaturation having from 1 to 40 carbon atoms. Monovalent hydrocarbon radicals free of aliphatic unsaturation which are suitable as $R'$ include alkyl radicals such as methyl, ethyl, propyl, butyl, hexyl, octyl, and decyl, cycloaliphatic radicals such as cyclohexyl, aryl radicals such as phenyl, tolyl, and xylyl, and arylalkyl radicals such as benzyl and phenylethyl.

Monovalent hydrocarbon radicals suitable as $R'$ also include arene radicals having from 6 to 40 carbon atoms such as naphthyl ($C_{10}H_7$), anthracenyl or phenanthracenyl ($C_{14}H_9$), pyrenyl ($C_{16}H_9$), napthacenyl, 9,10-benzophenanthrenyl, chrysenyl, 1,2-benzanthracenyl, or 3,4-benzophenanthrenyl ($C_{18}H_{11}$), 3,4-benzopyrene or perylenyl ($C_{20}H_{11}$), 1,2,3,4-dibenzanthracenyl, 1,2,5,6-dibenzanthracenyl, 1,2,6,7-dibenzoanthracenyl, 1,2,7,8-dibenzanthracenyl, 1,2,6,7-dibenzophenanthracenyl, 1,2,7,8-dibenzophenanthracenyl, pentacenyl, or picenyl ($C_{22}H_{13}$), coronenyl ($C_{24}H_{11}$), 1,2,4,5-dibenzopyrene ($C_{24}H_{13}$), and hexacenyl ($C_{26}H_{15}$). Arene radicals having up to 40 carbon atoms which are suitable as $R'$ also include combinations of the above radicals attached to one another such as phenylhexadecenyl ($C_{32}H_{19}$) or anthracenylhexacenyl ($C_{40}H_{23}$).

The group $R'$ can also be a halogen atom, or a radical selected from $NO_2$, $CN$, $COOH$, and $SO_3H$. Halogen atoms suitable as $R'$ include fluorine, chlorine, and bromine. Alkoxy radicals suitable as $R'$ include radicals such as methoxy, ethoxy, propoxy, and butoxy radicals. Nitro substituted groups suitable as $R'$ include groups such as $3\text{-}O_2N\text{---}C_6H_4$ or $4\text{-}Cl,3\text{-}O_2N\text{---}C_6H_3$. Nitrile substituted groups suitable as $R'$ are exemplified by groups such as $4\text{-}NC\text{---}C_6H_4$, $1\text{-}NC\text{---}C_{10}H_7$, or $2\text{-}NC\text{---}C_{10}H_7$. Carboxylic acid substituted groups suitable as $R'$ are exemplified by groups such as $4\text{-}HOOC\text{---}C_6H_4$ or $3\text{-}HOOC\text{---}C_6H_4$. Sulfonic acid substituted groups suitable as $R'$ are exemplified by groups such as $4\text{-}HO_3S\text{---}C_6H_4$ or $3\text{-}HO_3S\text{---}C_6H_4$. The alkoxy substituted groups suitable as $R'$ include groups such as $4\text{-}CH_3O\text{---}C_6H_4$, $4\text{-}C_2H_5O\text{---}C_6H_4$, $2\text{-}CH_3O\text{---}C_6H_4$, and $2\text{-}C_2H_5O\text{---}C_6H_4$.

The group $R''$ is a monovalent hydrocarbon or halohydrocarbon radical free of aliphatic unsaturation having from 1 to 20 carbon atoms. Monovalent hydrocarbon radicals free of aliphatic unsaturation which are suitable as $R''$ include alkyl radicals such as methyl, ethyl, propyl, butyl, hexyl, octyl, and decyl, cycloaliphatic radicals such as cyclohexyl, aryl radicals such as phenyl, tolyl, and xylyl, and arylalkyl radicals such as benzyl and phenylethyl.

Ar in the formula hereinabove denotes an aromatic radical having the formula $C_nH_{(n/2+2)}$ or of formula $C_mH_{(m/2+1)}$, wherein n has a value of 6, 10, 14, 18, 22, 26, 30, 34 or 38 and m has a value of 16, 20, 24, 28, 32, 36, or 40. Ar denotes arene radicals having from 6 to 40 carbon atoms. Arene radicals suitable as Ar are exemplified by phenyl ($C_6H_5$), naphthyl ($C_{10}H_7$), anthracenyl or phenanthracenyl ($C_{14}H_9$), pyrenyl ($C_{16}H_9$), napthacenyl, 9,10-benzophenanthrenyl, chrysenyl, 1,2-benzanthracenyl, or 3,4-benzophenanthrenyl ($C_{18}H_{11}$), 3,4-benzopyrene or perylenyl ($C_{20}H_{11}$), 1,2,3,4-dibenzanthracenyl, 1,2,5,6-dibenzanthracenyl, 1,2,6,7-dibenzoanthracenyl, 1,2,7,8-dibenzanthracenyl, 1,2,6,7-dibenzophenanthracenyl, 1,2,7,8-dibenzophenanthracenyl, pentacenyl, or picenyl ($C_{22}H_{13}$), coronenyl ($C_{24}H_{11}$), 1,2,4,5-dibenzopyrene ($C_{24}H_{13}$), hexacenyl ($C_{26}H_{15}$), and combinations of these radicals attached to one another such as phenylhexadecenyl ($C_{32}H_{19}$) or anthracenylhexacenyl ($C_{40}H_{23}$).

In step (I) of the method of this invention compound (A) delineated hereinabove is mixed with compound (B) a solvent selected from the group consisting of acetic acid, chlorinated hydrocarbons, and polar aprotic solvents. The chlorinated hydrocarbons are preferably selected from the group consisting of methylene chloride, chloroform, and 1,2-dichloroethane. Preferably the polar aprotic solvents are selected from the group consisting of acetonitrile, dimethylsulfoxide, and benzonitrile.

For purposes of this invention from 40 to 100 percent by weight of solvent (B) can be used, and it is preferred that from 90 to 100 percent by weight of (B) be employed, said percent by weight being based on the total weight of Components (A), (C), and (D).

Step (II) in the method of the present invention comprises adding to the mixture of (I) an acid (C) selected from the group consisting of perfluoroalkylsulfonic acids, hexahalometallic acids, hexahalometalloidic acids, tetrahaloboronic acids, tetrakis(perfluoroaryl)boronic acids, and tetrakisperfluoroalkylsulfonatoboronic acids at a temperature of at least −20° C. to form a homogenous reaction mixture. Perfluoroalkylsulfonic acids are exemplified by perfluorobutanesulfonic acid, perfluoroethanesulfonic acid, perfluoro-octanesulfonic acid, or trifluoromethanesulfonic acid. Hexahalometallic acids include acids such as $HSbF_6$, $HAsF_6$, $HSbCl_6$, and $HAsCl_6$, hexahalometalloidic acids include acids such as $HPF_6$ and $HPCl_6$, tetrahaloboronic acids include acids such as $HBF_4$, $HBCl_4$, and $HBBr_4$, tetrakis perfluoroaryl boronic acids are exemplified by $HB(C_6H_5)_4$ and $HB(C_{10}F_7)_4$, and tetrakisperfluoroalkylsulfonatoboronic acids include acids such as $HB(O_3SCF_3)_4$, $HB(O_3SC_2F_5)_4$, and $HB(O_3SC_4F_9)_4$. Preferably (C) is selected from the group consisting of trifluoromethanesulfonic acid, perfluorobutylsulfonic acid, hexafluoroantimonic acid, hexafluorophosphoric acid, hexafluoroarsenic acid, tetrafluoroboric acid, tetrakis(pentafluorophenyl)boric acid, and tetrakis(trifluoromethanesulfanato)boric acid.

Step (III) in the method of the present invention comprises reacting with the homogeneous reaction mixture of (II) a compound (D) selected from the group consisting of benzene, alkyl substituted benzenes, aryl substituted benzenes, arylalkyl substituted benzenes, alkoxy substituted benzenes, arylalkoxy substituted benzenes, and halobenzenes for at least 30 minutes. Preferably compound (D) is selected from the group consisting of benzene, toluene, xylene, butylbenzene, t-butylbenzene, dodecylbenzene, tetracosyl benzene, octylbenzene, 1-phenyl-5-methylheptane, bisdodecylbenzene, fluorobenzene, anisole, octyloxybenzene, dodecyloxybenzene, octadecyloxybenzene, 1-phenoxy-5-methylheptane, 1,2-bis(phenoxyethane), and 1,3-bis(2-phenylpropyl)-1,1,3,3-tetramethyldisiloxane.

Step (IV) in the method of the present invention comprises stripping off solvent from the mixture of (III). Methods of stripping volatile components are well known in the art and need no extensive delineation herein. Any method of removing volatile components can be used in the present invention, such methods exemplified by, but not limited to, distillation, evaporation, by passage of steam, air, or other gas through the liquid mixture, molecular stills, rotoevaporators, and wiped film evaporators. The preferred method of stripping off the solvent from the mixture of step (III) is by employing a rotoevaporator.

It is preferred for purposes of the present invention that the molar ratio of (A) to (C) to (D) is 0.95 to 1.05 to 0.95 to 1.05 to 0.95 to 1.05. It is preferred for purposes of the instant invention that the molar ratio of (A) to (C) to (D) is 1 to 1 to 1.

The method of the present invention can further comprise the step of adding a mixture of an organic solvent and water prior to step (IV) which results in the formation of an organic layer and an aqueous layer. The organic solvents suitable for the method of the present invention include methylene chloride, acetonitrile, mineral spirits, chlorinated hydrocarbons and the like, benzene, toluene, ethers, and xylene. Preferred organic solvents in the method of this invention include toluene and diethyl ether. The mixture of organic solvent and water can be added in a ratio of 99 weight percent organic solvent to 1 weight percent of water to a ratio of 1 weight percent organic solvent to 99 weight percent of water. It is preferred that the organic solvent make up at least 30 weight percent of this mixture. Addition of this mixture results in the formation of two layers, an organic layer and an aqueous layer. Separation of the organic layer and the aqueous layer comprises allowing the non-miscible layers to phase separate and then drawing the less dense layer of the top and the more dense layer off the bottom of a separation vessel. The manner in which the two layers are mechanically separated is not critical as long as the two layers are isolated. Separation of the two layers may be accomplished by any of the separation methods well known to those skilled in the art. Separation of the two layers may be accomplished by evaporation, distillation, drying, gas absorption, sedimentation, solvent extraction, press extraction, adsorption, and filtration.

The method of the present can further comprise adding water to the separated organic layer. The amount of water added to the organic layer is not critical and may be readily determined through routine experimentation by those of ordinary skill in the art. This can then be followed by stripping of the organic layer. Methods of stripping the organic layer are as delineated above.

The method of the present invention can further comprise heating the mixture after step (III). The mixture in this method of the invention is preferably heated at a temperature of about 20° C. to 100° C. and more highly preferred is that the mixture be heated at a temperature of from about 40° to 70° C. after step (III).

The diaryliodonium salts prepared by the method of the present invention are diaryliodonium salts having the general formula $R^i_aArI^+ArR^{ii}_bX^-$ wherein $R^i$ is selected from the group consisting of monovalent hydrocarbon or halohydrocarbon radicals free of aliphatic unsaturation having from 1 to 40 carbon atoms, halogen atoms, $NO_2$, CN, COOH, $SO_3H$, alkoxy radicals, nitro substituted groups, nitrile substituted groups, carboxylic acid substituted groups, sulfonic acid substituted groups, and alkoxy substituted groups, $R^{ii}$ is selected from the group consisting of monovalent hydrocarbon radicals free of aliphatic unsaturation and having from 1 to 40 carbon atoms, alkoxy substituted groups, arylalkoxy radicals, aryloxy radicals, and halogen atoms, Ar denotes arene radicals having from 6 to 40 carbon atoms, a has a value of from 0 to 10, b has value of from 0 to 10, and $X^-$ is an anion selected from the group consisting of perfluoroalkylsulfonic acid anions, hexahalometallic acid anions, hexahalometalloidic acid anions, tetrahaloboronic acid anions, tetrakis(perfluoroaryl)boronic acid anions, and tetrakisperfluoroalkylsulfonatoboronic acid anions.

Ar in the formula hereinabove denotes an aromatic radical having the formula $C_nH_{(n/2+2)}$ or of formula $C_mH_{(m/2+1)}$, wherein n has a value of 6, 10, 14, 18, 22, 26, 30, 34 or 38 and m has a value of 16, 20, 24, 28, 32, 36, or 40.

The group $R^i$ can be a monovalent hydrocarbon or halohydrocarbon radical free of aliphatic unsaturation having from 1 to 40 carbon atoms. Monovalent hydrocarbon radicals free of aliphatic unsaturation which are suitable as $R^i$ include alkyl radicals such as methyl, ethyl, propyl, butyl, hexyl, octyl, and decyl, cycloaliphatic radicals such as cyclohexyl, aryl radicals such as phenyl, tolyl, and xylyl, and arylalkyl radicals such as benzyl, phenylmethyl, phenylethyl, and phenylnaphthyl.

Monovalent hydrocarbon radicals suitable as $R^i$ also include arene radicals having from 6 to 40 carbon atoms such as naphthyl ($C_{10}H_7$), anthracenyl or phenanthracenyl ($C_{14}H_9$), pyrenyl ($C_{16}H_9$), napthacenyl, 9,10-benzophenanthrenyl, chrysenyl, 1,2-benzanthracenyl, or 3,4- benzophenanthrenyl ($C_{18}H_{11}$), 3,4-benzopyrene or perylenyl ($C_{20}H_{11}$), 1,2,3,4-dibenzanthracenyl, 1,2,5,6-dibenzanthracenyl, 1,2,6,7-dibenzoanthracenyl, 1,2,7,8-dibenzanthracenyl, 1,2,6,7-dibenzophenanthracenyl, 1,2,7,8dibenzophenanthracenyl, pentacenyl, or picenyl ($C_{22}H_{13}$), coronenyl ($C_{24}H_{11}$), 1,2,4,5-dibenzopyrene ($C_{24}H_{13}$), and hexacenyl ($C_{26}H_{15}$). Arene radicals having up to 40 carbon atoms which are suitable as $R^i$ also include combinations of the above radicals attached to one another such as phenylhexadecenyl ($C_{32}H_{19}$) or anthracenylhexacenyl ($C_{40}H_{23}$).

The group $R^i$ can also be a halogen atom, or a radical selected from $NO_2$, CN, COOH, and $SO_3H$. Halogen atoms suitable as R' include fluorine, chlorine, and bromine. Alkoxy radicals suitable as $R^i$ include radicals such as methoxy, ethoxy, propoxy, and butoxy radicals. Nitro substituted groups suitable as $R^i$ include groups such as $3\text{-}O_2N\text{---}C_6H_4$ or 4-Cl, $3\text{-}O_2N\text{---}C_6H_3$. Nitrile substituted groups suitable as $R^i$ are exemplified by groups such as $4\text{-}NC\text{---}C_6H_4$, $1\text{-}NC\text{---}C_{10}H_7$, or $2\text{-}NC\text{---}C_{10}H_7$. Carboxylic acid substituted groups suitable as $R^i$ are exemplified by groups such as $4\text{-}HOOC\text{---}C_6H_4$ or $3\text{-}HOOC\text{---}C_6H_4$. Sulfonic acid substituted groups suitable as $R^i$ are exemplified by groups such as $4\text{-}HO_3S\text{---}C_6H_4$ or $3\text{-}HO_3S\text{---}C_6H_4$. The alkoxy substituted groups suitable as $R^i$ include groups such as $4\text{-}CH_3O\text{---}C_6H_4$, $4\text{-}C_2H_5O\text{---}C_6H_4$, $2\text{-}CH_3O\text{---}C_6H_4$, and $2\text{-}C_2H_5O\text{---}C_6H_4$.

The monovalent hydrocarbon radicals free of aliphatic unsaturation having from 1 to 40 carbon atoms (including arene radicals having from 6 to 40 carbon atoms), alkoxy substituted groups, and halogen atoms suitable as $R^{ii}$ are as delineated above for $R^i$ including preferred embodiments thereof. Arylalkoxy radicals suitable as $R^{ii}$ include radicals such as benzyloxy and phenylethyloxy. Aryloxy radicals suitable as $R^{ii}$ are exemplified by radicals such as phenoxy and napthoxy.

Ar denotes arene radicals having from 6 to 40 carbon atoms. Arene radicals suitable as Ar are exemplified by phenyl ($C_6H_5$), naphthyl ($C_{10}H_7$), anthracenyl or phenanthracenyl ($C_{14}H_9$), pyrenyl ($C_{16}H_9$), napthacenyl, 9,10-benzophenanthrenyl, chrysenyl, 1,2-benzanthracenyl, or 3,4-benzophenanthrenyl ($C_{18}H_{11}$), 3,4-benzopyrene or perylenyl ($C_{20}H_{11}$), 1,2,3,4-dibenzanthracenyl, 1,2,5,6-dibenzanthracenyl, 1,2,6,7-dibenzoanthracenyl, 1,2,7,8-dibenzanthracenyl, 1,2,6,7-dibenzophenanthracenyl, 1,2,7,8-dibenzophenanthracenyl, pentacenyl, or picenyl ($C_{22}H_{13}$), coronenyl ($C_{24}H_{11}$), 1,2,4,5-dibenzopyrene ($C_{24}H_{13}$), hexacenyl ($C_{26}H_{15}$), and combinations of these radicals attached to one another such as phenylhexadecenyl ($C_{32}H_{19}$) or anthracenylhexacenyl ($C_{40}H_{23}$).

The anion $X^-$ can be an anion selected from the group consisting of perfluoroalkylsulfonic acid anions, hexahalometallic acid anions, hexahalometalloidic acid anions, tetrahaloboronic acid anions, tetrakis(perfluoroaryl)boronic acid anions, and tetrakisperfluoroalkylsulfonatoboronic acid anions. Perfluoroalkylsulfonic acid anions are exemplified by perfluorobutanesulfonic acid anions, perfluoroethanesulfonic acid anions, perfluoro-octanesulfonic acid anions, or trifluoromethanesulfonic acid anions. Hexahalometallic acid anions include anions such as $SbF_6^-$, $AsF_6^-$, $SbCl_6^-$, and $AsCl_6^-$, hexahalometalloidic acid anions include anions such as $PF_6^-$ and $PCl_6^-$, tetrahaloboronic acid anions include anions such as $BF_4^-$, $BCl_4^-$, and $BBr_4^-$, tetrakis perfluoroaryl boronic acid anions are exemplified by $B(C_6H_5)_4^-$ and $B(C_{10}F_7)_4^-$, and tetrakisperfluoroalkylsulfonatoboronic acid anions include anions such as $B(O_3SCF_3)_4^-$, $B(O_3SC_2F_5)_4^-$, and $B(O_3SC_4F_9)_4^-$. It is preferred that $X^-$ is trifluoromethanesulfonate.

The following examples are disclosed to further teach, but not limit, the invention which is properly delineated by the appended claims. All amounts (parts and percentages) are by weight unless otherwise indicated.

EXAMPLE 1

To a stirred suspension of 6.44 g (grams) (0.02 mole) of iodobenzene diacetate (from Aldrich, Madison, Wis.) in 20 ml of glacial acetic acid (Solvent) (from FISHER SCIENTIFIC, Pittsburgh, Pa.) was added 3.0 g (0.02 mole) trifluoromethanesulfonic acid (triflic acid, or TfOH, or HOTf) (FC-24 from 3M Co., Minneapolis, Minn.) in dropwise fashion while the solution was at ambient temperature. After all solids were completely dissolved and a clear yellow solution was obtained, there was added to this stirred yellow solution about 2.12 g of 1,3-xylene (Ar) (from Aldrich) in a dropwise fashion, also while the solution was at ambient temperature. The resulting mixture was allowed to stir for about 30 minutes. After this time the solvent was removed by evaporation on a rotary evaporator under an ultimate pressure of less than 1 mm Hg and at a bath temperature of less than 80° C. An oily residue was obtained. The residue was triturated with diethylether (crystallizing solvent) until it solidified, after which it was collected by filtration and washed with more diethyl ether and dried in vacuo. The product was collected in a crystalline form and in a 94% of theoretical yield.

Example 2

To a stirred suspension of 6.44 g (0.02 mole) iodobenzene diacetate (Aldrich, Madison, Wis.) in 20 ml glacial acetic acid (Solvent) (FISHER SCIENTIFIC, Pittsburgh, Pa.) was added 3.0 g (0.02 mole) trifluoromethanesulfonic acid (triflic acid, or TfOH, or HOTf) (FC-24 from 3M Co, Minneapolis, Minn.) in dropwise fashion while the solution was at ambient temperature. After all solids were completely dissolved and a clear yellow solution was obtained, there was added to this stirred yellow solution about 4.92 g of dodecylbenzene (Ar) (from Johnson Matthey Catalog Co., INC, Ward Hill, Mass.) in a dropwise fashion while the solution was at ambient temperature. The resulting mixture was allowed to stir for about 3 hours. Acetic acid was then removed in a rotary evaporator leaving a reaction mixture of oil and acetic acid. After this time there was added to the reaction mixture about 30 ml of toluene (from FISHER) and 30 ml deionized water and the resulting aqueous and organic layers were separated. The organic layer was subsequently repeatedly washed with further portions of deionized water until the pH of the separated water layer was greater than 5. The toluene solvent and residual water was then removed from the separated organic layer by evaporation on a rotary evaporator under an ultimate pressure of less than 1 mm Hg and at a bath temperature of less than 80° C. The product was a residue from this separation process in the form of a viscous liquid oil. The oil was converted to a low-melting solid product, in the case of dodecylbenzene as the substrate, by dissolving the viscous oil in toluene and then adding the solution to an excess of n-pentane and recovering the precipitated solids formed thereby by means of filtration, washing the precipitate with more clean pentane, and then drying in vacuo.

However, the viscous oil was a perfectly suitable form of the product.

Example 3

To a stirred suspension of 6.44 g (0.02 mole) iodobenzene diacetate (Aldrich, Madison, Wis.) in 20 ml glacial acetic acid (Solvent) (FISHER SCIENTIFIC, Pittsburgh, Pa.) was added 3.0 g (0.02 mole) trifluoromethanesulfonic acid (triflic acid, or TfOH, or HOTf) (FC-24 from 3M Co, Minneapolis, Minn.) in dropwise fashion while the solution was at ambient temperature. After all solids were completely dissolved and a clear yellow solution was obtained, there was added to this stirred yellow solution about 4.92 g of dodecylbenzene (Ar) (from Johnson Matthey Catalog Co., INC, Ward Hill, Mass.) in a dropwise fashion while the solution was at ambient temperature. The resulting mixture was allowed to stir for about 3 hours. Acetic acid was then removed in a rotary evaporator leaving a reaction mixture of oil and acetic acid. After this time there was added to the reaction mixture about 30 ml of toluene (from FISHER) and 30 ml deionized water and this mixture was agitated to allow the acetic acid to mix with the water phase. The water phase was then drawn off the top and more fresh water was added. The procedure was repeated several times until acetic acid could not be detected in the water phase. The toluene solvent and residual water were then removed from the separated organic layer by evaporation on a rotary evaporator under an ultimate pressure of less than 1 mm Hg and at a bath temperature of less than 80° C. The product was a residue from this separation process in the form of a viscous liquid oil at stripping temperatures but was a solid waxy substance at room temperature. The solid was further purified, in the case of dodecylbenzene as the substrate, by dissolving the solid product in toluene and then adding this solution to an excess of n-pentane and recovering the precipitated solids formed thereby by means of filtration, washing the precipitate with more clean pentane, and then drying in vacuo.

Examples 4–45

In the examples hereinbelow, the above procedure' was utilized. In Table I is delineated amount of iodobenzene diacetate, solvent type, solvent amount, amount of trifluoromethanesulfonic acid (denoted FC-24), aromatic compound type (Ar), and amount of Ar. Mixing times ranged from an hour to several hours, and mixing temperatures were at room temperature or ranged from 45° to 70° C. Where a crystallizing solvent was employed, the procedure of Example 1 was followed, where no crystallizing solvent was used, the procedure of Example 2 was employed, and where the oil is reported as being in the form of a solid then the procedure of Example 3 was followed. Table II hereinbelow describes the amount of oil produced (product), oil color, crystallizing solvent (if used), product obtained, and the percent of theoretical yield obtained. In the Examples hereinbelow triflate denotes trifluoromethanesulfonate. The identity of the obtained product was determined by NMR (Nuclear Magnetic Resonance) and IR (Infrared Spectroscopy).

TABLE I

| | | Iodobenzene Diacetate (g) | Solvent | Solvent (ml) | FC-24 (g) | Ar | Ar (g) |
|---|---|---|---|---|---|---|---|
| Ex. | 4 | 9.66 | HOAc | 20 | 4.51 | benzene | 2.35 |
| | 5 | 6.44 | HOAc | 20 | 3.00 | benzene | 1.56 |
| | 6 | 3.24 | HOAc | 20 | 1.48 | toluene | 0.91 |
| | 7 | 3.22 | HOAc | 20 | 1.51 | m-xylene | 1.07 |
| | 8 | 3.29 | HOAc | 20 | 1.52 | pentamethylbenzene | 1.49 |
| | 9 | 6.44 | HOAc | 20 | 3.00 | n-butylbenzene | 2.68 |
| | 10 | 3.23 | HOAc | 20 | 1.50 | sec-butylbenzene | 1.37 |
| | 11 | 3.25 | HOAc | 20 | 1.50 | tert-butylbenzene | 1.34 |
| | 12 | 3.24 | HOAc | 20 | 1.51 | phenylcyclohexane | 1.60 |
| | 13 | 6.47 | HOAc | 20 | 3.02 | 1-phenylhexane | 3.26 |
| | 14 | 9.69 | HOAc | 20 | 4.52 | dodecylbenzene | 7.40 |
| | 15 | 6.43 | HOAc | 20 | 3.00 | dodecylbenzene | 4.94 |
| | 16 | 9.67 | HOAc | 20 | 4.50 | dodecylbenzene | 7.39 |
| | 17 | 9.68 | HOAc | 20 | 4.50 | dodecylbenzene | 7.40 |
| | 18 | 9.72 | HOAc | 20 | 4.53 | dodecylbenzene | 7.42 |
| | 19 | 9.66 | HOAc | 20 | 4.52 | dodecylbenzene | 7.40 |
| | 20 | 9.68 | CH2Cl2 | 20 | 4.52 | dodecylbenzene | 7.41 |
| | 21 | 6.46 | HOAc | 20 | 3.00 | dodecylbenzene | 4.93 |
| | *22 | 6.75 | HOAc | 20 | 3.15 | 1-phenyldodecane | 5.17 |
| | 23 | 6.76 | HOAc | 20 | 3.02 | benzene | 1.56 |
| | 24 | 6.44 | HOAc | 20 | 3.01 | fluorobenzene | 1.93 |
| | 25 | 9.68 | HOAc | 20 | 4.51 | chlorobenzene | 3.38 |
| | 26 | 6.44 | HOAc | 20 | 3.02 | iodobenzene | 4.10 |
| | 27 | 6.44 | HOAc | 20 | 3.02 | 3-iodotoluene | 4.37 |
| | 28 | 3.23 | HOAc | 25 | 1.49 | methylphenylether | 1.01 |
| | 29 | 3.22 | CH3CN | 25 | 1.48 | methylphenylether | 1.10 |
| | 30 | 3.24 | CH2Cl2 | 25 | 1.51 | methylphenylether | 1.11 |
| | 31 | 3.24 | HOAc | 20 | 1.51 | methylphenylether | 1.09 |
| | 32 | 3.22 | CH2Cl2 | 25 | 1.51 | methylphenylether | 1.13 |
| | 33 | 3.22 | CH3CN | 25 | 1.50 | methylphenylether | 1.10 |
| | 34 | 3.22 | HOAc | 20 | 1.51 | butylphenylether | 1.50 |
| | 35 | 12.88 | HOAc | 50 | 6.47 | octylphenylether | 8.65 |
| | 36 | 3.24 | HOAc | 20 | 1.50 | octadecylphenylether | 3.46 |
| | 37 | 6.44 | HOAc | 20 | 3.01 | 4-phenoxybutyl bromide | 4.58 |
| | 38 | 6.43 | CH2Cl2 | 20 | 3.00 | 2-phenoxyethanol | 2.77 |
| | 39 | 6.45 | HOAc | 20 | 3.00 | 2-phenoxyethanol | 2.76 |
| | 40 | 6.46 | CH2Cl2 | 20 | 3.00 | 2-phenoxyethanol | 2.77 |
| | 41 | 12.89 | HOAc | 20 | 6.01 | 2-phenoxyethanol | 5.54 |
| | 42 | 12.86 | HOAc | 50 | 6.00 | 2-phenoxyethanol | 5.53 |
| | 43 | 6.46 | HOAc | 20 | 3.02 | thiophene | 1.68 |
| | 44 | 9.73 | HOAc | 20 | 4.52 | dodecylbenzene | 7.41 |

TABLE I-continued

| Diacetate | Iodobenzene (g) | Solvent | Solvent (ml) | FC-24 (g) | Ar | Ar (g) |
|---|---|---|---|---|---|---|
| 45 | 10.08 | HOAc | 20 | 4.50 | dodecylbenzene | 7.39 |

*3-Iodotoluene Diacetate was substituted for Iodobenzene Diacetate

*-3-Iodotoluene Diacetate was substituted for Iodobenzene Diacetate

TABLE II

| Ex. | Oil (g) | Oil Color | Crystallizing Solvent | % Yield | Product Obtained |
|---|---|---|---|---|---|
| 4 | 10.80 | orange | ether | 59.5 | Diphenyliodonium triflate |
| 5 | 8.69 | yellow | ether | 50.0 | Diphenyliodonium triflate |
| 6 | 4.92 | yellow | ether | 51.6 | 4-methylphenylphenyl iodonium triflate |
| 7 | 5.35 | white | ether | 93.3 | dimethylphenylphenyl iodonium triflate |
| 8 | 4.44 | dark purple | ether | 23.5 | pentamethylphenylphenyl iodonium triflate |
| 9 | 10.45 | brown | ether | 58.4 | butylphenylphenyl iodonium triflate |
| 10 | 5.72 | yellow | ether | 58.2 | s-butylphenylphenyl iodonium triflate |
| 11 | 5.49 | yellow | ether | 45.8 | t-butylphenylphenyl iodonium triflate |
| 12 | 6.15 | yellow | ether | 51.6 | cyclohexylphenylphenyl iodonium triflate |
| 13 | 10.68 | brown | none | 73.8 | hexylphenylphenyl iodonium triflate |
| 14 | 20.01 | yellow | none | 80.6 | dodecylphenylphenyl iodonium triflate |
| 15 | 12.57 | brown | none | 80.2 | dodecylphenylphenyl iodonium triflate |
| 16 | 18.61 | brown | none | 79.2 | dodecylphenylphenyl iodonium triflate |
| 17 | 20.10 | yellow | none | 78.8 | dodecylphenylphenyl iodonium triflate |
| 18 | 19.45 | yellow | none | 78.6 | dodecylphenylphenyl iodonium triflate |
| 19 | 18.97 | orange | none | 72.0 | dodecylphenylphenyl iodonium triflate |
| 20 | 18.61 | orange | none | 69.0 | dodecylphenylphenyl iodonium triflate |
| 21 | 12.30 | orange | none | 47.5 | dodecylphenylphenyl iodonium triflate |
| 22 | 12.08 | brown | none | 76.3 | dodecylphenylphenyl iodonium triflate |
| 23 | 8.32 | yellow-orange | ether | 53.2 | 3-methylphenylphenyl iodonium triflate |
| 24 | 8.86 | orange | ether | 68.8 | 4-fluorophenylphenyl iodonium triflate |
| 25 | 13.27 | orange | ether | 40.2 | 4-chlorophenylphenyl iodonium triflate |
| 26 | 8.66 | orange | ether | 52.8 | 4-iodophenylphenyl iodonium triflate |
| 27 | 10.96 | orange | ether | 50.9 | iodotolylphenyl iodonium triflate |
| 28 | 4.15 | red-brown | CH2Cl2-ether | 56.3 | methoxyphenylphenyl iodonium triflate |
| 29 | 3.19 | brown | ether | 54.5 | methoxyphenylphenyl iodonium triflate |
| 30 | 3.39 | brown | ether | 53.5 | methoxyphenylphenyl iodonium triflate |
| 31 | 5.75 | dark brown | ether | 50.9 | methoxyphenylphenyl iodonium triflate |
| 32 | 2.37 | red-brown | CH2Cl2-ether | 21.7 | methoxyphenylphenyl iodonium triflate |
| 33 | 1.79 | red-brown | CH2Cl2-ether | 15.4 | methoxyphenylphenyl iodonium triflate |
| 34 | 5.14 | black-green | ether | 61.1 | butyloxyphenylphenyl iodonium triflate |
| 35 | 18.98 | brown | none | 67.0 | octyloxyphenylphenyl iodonium triflate |
| 36 | 12.79 | dark brown | ether | 73.0 | 3bromopropoxyphenylphenyl iodonium triflate |
| 37 | 11.93 | brown | ether | 82.6 | 4-(4'-bromobutoxy)phenylphenyl iodonium triflate |
| 38 | 10.88 | brown | ether | 71.8 | 4-(2-hydroxyethoxy)phenylphenyl |

TABLE II-continued

| Ex. | Oil (g) | Oil Color | Crystallizing Solvent | % Yield | Product Obtained |
|---|---|---|---|---|---|
| 39 | 11.42 | dark brown | ether | 71.3 | 4-(2-hydroxyethoxy) phenylphenyl iodonium triflate |
| 40 | 13.45 | brown | ether | 71.3 | 4-(2-hydroxyethoxy) phenylphenyl iodonium triflate |
| 41 | 20.40 | brown | ether | 58.3 | 4-(2-hydroxyethoxy) phenylphenyl iodonium triflate |
| 42 | 20.97 | brown | ether | 7.1 | 4-(2-hydroxyethoxy) phenylphenyl iodonium triflate |
| 43 | 10.35 | dark blue | ether | 8.2 | 2-thiophenylphenyl iodonium triflate |
| 44 | solid | yellow | none | 93.0 | Dodecylphenyphenyl iodonium triflate |
| 45 | solid | yellow | none | 94.8 | (Dodecylphenyl) (3-methylphenyl) iodonium triflate |

It should be apparent from the foregoing that many other variations and modifications may be made in the compounds, compositions and methods described herein without departing substantially from the essential features and concepts of the present invention. Accordingly it should be clearly understood that the forms of the invent/on described herein are exemplary only and are not intended as limitations on the scope of the present invention as defined in the appended claims.

That which is claimed is:

1. A method for the preparation of iodonium salts, the method comprising the steps of:

(I) mixing (A) substituted or unsubstituted iodoarene dicarboxylates and (B) a solvent selected from the group consisting of acetic acid, chlorinated hydrocarbons, and polar aprotic solvents;

(II) adding to the mixture of (I) an acid (C) selected from the group consisting of perfluoroalkylsulfonic acids, hexahalometallic acids, hexahalometalloidic acids, tetrahaloboronic acids, tetrakis(perfluoroaryl)boronic acids, and tetrakisperfluoroalkylsulfonatoboronic acids at a temperature of at least $-20°$ C. to form a homogenous reaction mixture;

(III) reacting with the homogeneous reaction mixture of (II) a compound (D) selected from the group consisting of benzene, alkyl substituted benzenes, aryl substituted benzenes, arylalkyl substituted benzenes, alkoxy substituted benzenes, arylalkoxy substituted benzenes, and halobenzenes for at least 30 minutes; and (IV) stripping off solvent from the mixture of (III).

2. A method according to claim 1, wherein (A) is a compound having the formula $R'_aArI(O_2CR'')_2$ wherein $R'$ is selected from the group consisting of monovalent hydrocarbon radicals or halohydrocarbon radicals free of aliphatic unsaturation having from 1 to 40 carbon atoms, halogen atoms, $NO_2$, CN, COOH, $SO_3H$, alkoxy radicals, nitro substituted groups, nitrile substituted groups, carboxylic acid substituted groups, sulfonic acid substituted groups, alkoxy substituted groups, $R''$ is a monovalent hydrocarbon or halohydrocarbon radicals free of aliphatic unsaturation having from 1 to 20 carbon atoms, a has a value of from 0 to 10, and Ar denotes an arene radical having from 6 to 40 carbon atoms.

3. A method according to claim 2, wherein the monovalent hydrocarbon radicals having from 1 to 40 carbon atoms are selected from the group consisting of methyl, ethyl, propyl, butyl, hexyl, octyl, decyl, cyclohexyl, phenyl, tolyl, xylyl, benzyl, phenylmethyl, phenylethyl, phenylnaphthyl, naphthyl, anthracenyl, phenanthracenyl, pyrenyl, napthacenyl, 9,10-benzophenanthrenyl, chrysenyl, 1,2-benzanthracenyl, 3,4-benzophenanthrenyl, 3,4-benzopyrene, perylenyl, 1,2,3,4-dibenzanthracenyl, 1,2,5,6-dibenzanthracenyl, 1,2,6,7-dibenzoanthracenyl, 1,2,7,8-dibenzanthracenyl, 1,2,6,7-dibenzophenanthracenyl, 1,2,7,8-dibenzophenanthracenyl, pentacenyl, picenyl, coronenyl, 1,2,4,5-dibenzopyrene, hexacenyl, phenylhexadecenyl, and anthracenylhexacenyl.

4. A method according to claim 2, wherein the halogen atoms are selected from the group consisting of fluorine, chlorine, and bromine.

5. A method according to claim 2, wherein the alkoxy radicals are selected from the group consisting of methoxy, ethoxy, propoxy, and butoxy.

6. A method according to claim 2, wherein the nitro substituted groups are selected from the group consisting of $3-O_2N-C_6H_4$ and $4-Cl,3-O_2N-C_6H_3$.

7. A method according to claim 2, wherein the nitrile substituted groups are selected from the group consisting of $4-NC-C_6H_4$, $1-NC-C_{10}H_7$, and $2-NC-C_{10}H_7$.

8. A method according to claim 2, wherein the carboxylic acid substituted groups are selected from the group consisting of $4-HOOC-C_6H_4$ and $3-HOOC-C_6H_4$.

9. A method according to claim 2, wherein the sulfonic acid substituted groups are selected from the group consisting of $4-HO_3S-C_6H_4$ and $3-HO_3S-C_6H_4$.

10. A method according to claim 2, wherein the alkoxy substituted groups are selected from the group consisting of $4-CH_3O-C_6H_4$, $4-C_2H_5O-C_6H_4$, $2-CH_3O-C_6H_4$, and $2-C_2H_5O-C_6H_4$.

11. A method according to claim 2, wherein $R''$ is selected from the group consisting of methyl, ethyl, propyl, butyl, hexyl, octyl, decyl, cyclohexyl, phenyl, tolyl, xylyl, benzyl, phenylethyl, and phenylnaphthyl.

12. A method according to claim 2, wherein the arene radical is selected from the group consisting of phenyl, naphthyl, anthracenyl, phenanthracenyl, pyrenyl, napthacenyl, 9,10-benzophenanthrenyl, chrysenyl, 1,2-benzanthracenyl, 3,4-benzophenanthrenyl, 3,4-benzopyrene, perylenyl, 1,2,3,4-dibenzanthracenyl, 1,2,5,6-dibenzanthracenyl, 1,2,6,7-dibenzoanthracenyl, 1,2,7,8-dibenzanthracenyl, 1,2,6,7-dibenzophenanthracenyl, 1,2,7,8-dibenzophenanthracenyl, pentacenyl, picenyl, coronenyl, 1,2,4,5-dibenzopyrene, hexacenyl, phenylhexadecenyl, and anthracenylhexacenyl.

13. A method according to claim 1, wherein the chlorinated hydrocarbons are selected from the group consisting of methylene chloride, chloroform, and 1,2-dichloroethane.

14. A method according to claim 1, wherein the polar aprotic solvent is selected from the group consisting of acetonitrile, dimethylsulfoxide, and benzonitrile.

15. A method according to claim 1, wherein (C) is selected from the group consisting of trifluoromethanesulfonic acid, perfluorobutylsulfonic acid, hexafluoroantimonic acid, hexafluorophosphoric acid, hexafluoroarsenic acid, tetrafluoroboric acid, tetrakis(pentafluorophenyl)boric acid, and tetrakis(trifluoromethanesulfanato)boric acid.

16. A method according to claim 1, wherein (D) is selected from the group consisting of benzene, toluene, xylenes, butylbenzene, t-butylbenzene, dodecylbenzene, tetracosyl benzene, octylbenzene, 1-phenyl-5-methylheptane, bisdodecylbenzene, fluorobenzene, anisole, octyloxybenzene, dodecyloxybenzene, octadecyloxybenzene, 1-phenoxy-5-methylheptane, 1,2-bis(phenoxyethane), and 1,3-bis(2-phenylpropyl)-1,1,3,3-tetramethyldisiloxane.

17. A method according to claim 1, wherein the method further comprises the step of adding a mixture of an organic solvent and water prior to step (IV) which results in the formation of an organic layer and an aqueous layer.

18. A method according to claim 17, wherein the method further comprises adding water to the organic layer.

19. A method according to claim 18, wherein the method further comprises stripping the organic layer.

20. A method according to claim 1, wherein the method further comprises heating the mixture after step (III).

* * * * *